(12) United States Patent
Giles et al.

(10) Patent No.: US 10,101,297 B2
(45) Date of Patent: Oct. 16, 2018

(54) OPTIMISED ION MOBILITY SEPARATION TIMESCALES FOR TARGETED IONS

(71) Applicant: Micromass UK Limited, Wilmslow (GB)

(72) Inventors: Kevin Giles, Stockport (GB); Steven Derek Pringle, Hoddlesden (GB); Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/383,700

(22) Filed: Dec. 19, 2016

(65) Prior Publication Data

US 2017/0102361 A1    Apr. 13, 2017

Related U.S. Application Data

(63) Continuation of application No. 14/772,467, filed as application No. PCT/GB2014/050648 on Mar. 5, 2014, now Pat. No. 9,523,658.

(30) Foreign Application Priority Data

Mar. 6, 2013 (EP) .................................... 13158047
Mar. 6, 2013 (GB) .................................. 1304037.3

(51) Int. Cl.
| | |
|---|---|
| *G01N 27/62* | (2006.01) |
| *H01J 49/00* | (2006.01) |
| *H01J 49/02* | (2006.01) |
| *H01J 49/06* | (2006.01) |
| *H01J 49/40* | (2006.01) |

(52) U.S. Cl.
CPC .......... *G01N 27/622* (2013.01); *H01J 49/004* (2013.01); *H01J 49/02* (2013.01); *H01J 49/062* (2013.01); *H01J 49/40* (2013.01)

(58) Field of Classification Search
USPC .............................. 250/283, 281, 282, 286
See application file for complete search history.

(56) References Cited

U.S. PATENT DOCUMENTS

| | | | |
|---|---|---|---|
| 6,744,043 B2 | 6/2004 | Loboda | |
| 6,794,641 B2 | 9/2004 | Bateman et al. | |
| 7,077,944 B2 | 7/2006 | Clemmer | |
| 7,095,013 B2 | 8/2006 | Bateman et al. | |
| 7,196,324 B2 | 3/2007 | Verentchikov | |
| 8,299,422 B2 | 10/2012 | Bateman et al. | |
| 8,426,802 B2 | 4/2013 | Giles et al. | |
| 8,541,737 B2 | 9/2013 | Ibrahim et al. | |

(Continued)

FOREIGN PATENT DOCUMENTS

| | | |
|---|---|---|
| EP | 1367633 | 12/2003 |
| EP | 1378930 | 1/2004 |

*Primary Examiner* — Kiet T Nguyen

(57) ABSTRACT

An analytical device for analyzing ions is provided comprising a separator for separating ions according to a physico-chemical property and an interface comprising one or more ion guides. A quadrupole rod set mass filter is arranged downstream of the interface. A control system is arranged and adapted: (i) to transmit a first group of ions which emerges from the separator through the interface with a first transit time t1; and (ii) to transmit a second group of ions which subsequently emerges from the separator through the interface with a second different transit time t2.

22 Claims, 3 Drawing Sheets

(56) References Cited

U.S. PATENT DOCUMENTS

| | | |
|---|---|---|
| 9,570,279 B2 * | 2/2017 | Hotta ................... H01J 37/05 |
| 2015/0034813 A1 | 2/2015 | Brown et al. |
| 2016/0163530 A1 | 6/2016 | Syage |
| 2016/0336161 A1 * | 11/2016 | Grothe, Jr. ............ H01J 49/025 |

* cited by examiner

OPTIMISED ION MOBILITY SEPARATION TIMESCALES FOR TARGETED IONS

CROSS-REFERENCE TO RELATED APPLICATIONS

This application is a continuation application of U.S. patent application Ser. No. 14/772,467, which is the National Stage of International Application No. PCT/GB2014/050648, filed 5 Mar. 2014, which claims priority from and the benefit of United Kingdom patent application No. 1304037.3 filed on 6 Mar. 2013 and European patent application No. 13158047.4 filed 6 Mar. 2013. The entire contents of these applications are incorporated herein by reference.

BACKGROUND OF THE PRESENT INVENTION

The present invention relates to an analytical device, a mass spectrometer, a method of analysing ions and a method of mass spectrometry. The preferred embodiment relates to an ion mobility separator ("IMS") which is coupled to and arranged upstream of a quadrupole rod set mass filter.

The timescales associated with ion mobility separators or spectrometers ("IMS") present practical difficulties such as the ability of a resolving quadrupole ("Q") arranged downstream of an ion mobility spectrometer to switch between transmitting different components in a single ion mobility spectrometer or separator experiment or cycle.

A particular problem with conventional mass spectrometers comprising an ion mobility spectrometer arranged upstream of a quadrupole mass filter is that the ion mobility separation timescales (e.g. 200 µs) of closely eluting analyte ions from the ion mobility spectrometer can be too fast for the quadrupole which may take e.g. 1 ms to switch mass to charge ratio transmission windows. As a result, the ion mobility spectrometer places significant limitations on system performance such as the dynamic range of ion detectors in a mass spectrometer comprising an ion mobility spectrometer, a quadrupole mass filter and a Time of Flight mass analyser.

US 2002/0070338 (Loboda) discloses in FIG. 5 an ion mobility section 66 and a quadrupole rod set 78 arranged upstream of a time of flight mass analyser 90.

WO 02/07185 (Clemmer) discloses in FIG. 17 an arrangement wherein an ion mobility spectrometer 34 is arranged upstream of a time of flight mass analyser 36.

US 2005/0242279 (Verentchikov) discloses a tandem time of flight mass spectrometer.

US 2011/0127417 (Ibrahim) discloses a system and method for collisional activation of charged particles.

GB 2497958 (Makarov) discloses a collision cell for tandem mass spectrometry.

GB-2391697 (Micromass) discloses a mass spectrometer having an ion guide which receives ions and emits ions in a synchronised manner with an orthogonal acceleration Time of Flight mass analyser.

GB-2397433 (Micromass) discloses a mass spectrometer wherein ions from a pulsed ion source are received by an ion guide in which multiple trapping regions are created.

GB-2451149 (Micromass) discloses a dual mode ion mobility mass analyser device.

GB-2421840 (Micromass) discloses a mass spectrometer comprising an ion guide located downstream of an ion mobility spectrometer.

GB-2485667 (Micromass) discloses a mass spectrometer comprising a gas phase ion-neutral reaction device arranged to perform Hydrogen-Deuterium exchange.

It is desired to provide an improved mass spectrometer and method of mass spectrometry.

SUMMARY OF THE PRESENT INVENTION

According to an aspect of the present invention there is provided an analytical device for analysing ions comprising:
a separator for separating ions according to a physico-chemical property;
an interface comprising one or more ion guides, each ion guide comprising a plurality of electrodes;
a quadrupole rod set mass or mass to charge ratio filter arranged downstream of the interface; and
a control system arranged and adapted:
(i) to transmit a first group of ions which emerges from the separator through the interface with a first transit time t1; and
(ii) to transmit a second group of ions which subsequently emerges from the separator through the interface with a second different transit time t2.

US 2002/0070338 (Loboda) does not disclose providing an interface between an ion mobility spectrometer and a quadrupole mass filter and arranging to transmit groups of ions which emerge from the ion mobility spectrometer through the interface with different transit times so as to allow a relatively fast ion mobility spectrometer to be coupled to a relatively slow quadrupole mass filter.

The preferred embodiment of the present invention alleviates some of the drawbacks associated with the fast separation timescales of ion mobility devices and in particular enables a relatively fast separator such as an ion mobility spectrometer or separator device (or other separators) to be interfaced to a slower device such as a quadrupole mass filter.

Optimised ion mobility separation timescales for targeted ions is a new mode of operation implementable on existing and future ion mobility spectrometer or separator based instruments.

The present invention enables the experimental timescales of ions separated by ion mobility and then filtered by mass to charge ratio to be altered so as to improve the performance of the system as a whole.

The present invention may be extended to other embodiments wherein the quadrupole rod set mass filter may be replaced by another ion-optical device or component. The ion-optical device or component preferably has a slower response time than the separation time of two closely eluting ions which are separated temporally by the upstream separator. It should be understood, therefore, that the provision of a quadrupole rod set mass filter although desirable is not essential to the present invention.

According to an aspect of the present invention there is provided an analytical device for analysing ions comprising:
a separator for separating ions according to a physico-chemical property;
an interface; and
a control system arranged and adapted:
(i) to transmit a first group of ions which emerges from the separator through the interface with a first transit time t1; and
(ii) to transmit a second group of ions which subsequently emerges from the separator through the interface with a second different transit time t2.

The physico-chemical property preferably comprises ion mobility or differential ion mobility.

The separator preferably comprises an ion mobility separator or a differential ion mobility separator.

The physico-chemical property preferably comprises mass or mass to charge ratio.

The separator preferably comprises a time of flight region.

The control system is preferably arranged and adapted to transmit the second group of ions through the interface with a transit time t2, wherein t2>t1.

The interface preferably comprises one or more ion guides, each ion guide comprising a plurality of electrodes.

The control system is preferably further arranged and adapted to apply one or more transient DC voltages or potentials to the plurality of electrodes so that the first group of ions are translated along the one or more ion guides with a first velocity.

The control system is preferably further arranged and adapted to apply one or more transient DC voltages or potentials to the plurality of electrodes so that the second group of ions are translated along the one or more ion guides with a second different velocity.

The second velocity is preferably slower than the first velocity.

The control system is preferably further arranged and adapted to maintain at a first time a first DC voltage or potential gradient along the one or more ion guides so that the first group of ions are urged along the one or more ion guides with a first velocity.

The control system is preferably further arranged and adapted to maintain at a second later time a second DC voltage or potential gradient along the one or more ion guides so that the second group of ions are urged along the one or more ion guides with a second different velocity.

The second DC voltage or potential gradient is preferably less than the first DC voltage or potential gradient.

The analytical device preferably further comprises a filter arranged downstream of the interface. The filter preferably comprises a mass or mass to charge ratio filter. The filter preferably comprises a quadrupole rod set mass or mass to charge ratio filter.

The control system is preferably further arranged and adjusted:

(i) to cause the mass or mass to charge ratio filter to transmit ions having masses or mass to charge ratios within a first mass or mass to charge ratio range; and then (ii) to cause the mass or mass to charge ratio filter to transmit ions having masses or mass to charge ratios within a second different mass or mass to charge ratio range.

The filter preferably comprises an ion mobility or differential ion mobility filter.

The control system is preferably further arranged and adjusted:

(i) to cause the ion mobility or differential ion mobility filter to transmit ions having an ion mobility or differential ion mobility within a first ion mobility or differential ion mobility range; and then (ii) to cause the ion mobility or differential ion mobility filter to transmit ions having an ion mobility or differential ion mobility within a second different ion mobility or differential ion mobility range.

The control system is preferably arranged and adapted to transmit the first group of ions which emerges from the separator through the interface with a first transit time t1 and to transmit the second group of ions which subsequently emerges from the separator through the interface with a second different transit time t2 within or during a single cycle of separation of ions within the separator.

According to an aspect of the present invention there is provided a mass spectrometer comprising an analytical device as described above.

According to an aspect of the present invention there is provided a method of analysing ions comprising:

separating ions according to a physico-chemical property in a separator;

providing an interface comprising one or more ion guides, each ion guide comprising a plurality of electrodes and a quadrupole rod set mass or mass to charge ratio filter arranged downstream of said interface;

transmitting a first group of ions which emerges from the separator through the interface with a first transit time t1; and transmitting a second group of ions which subsequently emerges from the separator through the interface with a second different transit time t2.

The steps of transmitting the first group of ions which emerges from the separator through the interface with a first transit time t1 and transmitting the second group of ions which subsequently emerges from the separator through the interface with a second different transit time t2 are preferably performed within or during a single cycle of separation of ions within the separator.

According to an aspect of the present invention there is provided method of mass spectrometry comprising a method as described above.

According to an aspect of the present invention there is provided an analytical device for analysing ions comprising:

a separator for separating ions according to a physico-chemical property;

an interface; and a control system arranged and adapted:

(i) to transmit a first group of ions which emerges from the separator through a first ion path through the interface with a first transit time t1; and (ii) to transmit a second group of ions which subsequently emerges from the separator through a second different (e.g. longer) ion path through the interface with a second different transit time t2.

The control system is preferably arranged and adapted to transmit the first group of ions which emerges from the separator through a first ion path through the interface with a first transit time t1 and to transmit a second group of ions which subsequently emerges from the separator through a second different (e.g. longer) ion path through the interface with a second different transit time t2 within or during a single cycle of separation of ions within the separator.

According to an aspect of the present invention there is provided a method of analysing ions comprising:

separating ions according to a physico-chemical property in a separator;

providing an interface;

transmitting a first group of ions which emerges from the separator through a first ion path through the interface with a first transit time t1; and transmitting a second group of ions which subsequently emerges from the separator through a second different (e.g. longer) ion path through the interface with a second different transit time t2.

The steps of transmitting the first group of ions which emerges from the separator through a first ion path through the interface with a first transit time t1 and transmitting a second group of ions which subsequently emerges from the separator through a second different (e.g. longer) ion path through the interface with a second different transit time t2 are preferably performed within or during a single cycle of separation of ions within the separator.

According to an aspect of the present invention there is provided an analytical device for analysing ions comprising:

a separator for separating ions according to a physico-chemical property;

an interface; and a control system arranged and adapted within a single cycle of separation of ions within the separator to transmit a first group of ions which emerges from the separator through the interface with a first transit time t1 and to transmit a second group of ions which subsequently emerges from the separator through the interface with a second different transit time t2.

According to an aspect of the present invention there is provided a method of analysing ions comprising:

separating ions according to a physico-chemical property in a separator; providing an interface; and during a single cycle of separation of ions within the separator transmitting a first group of ions which emerges from the separator through the interface with a first transit time t1 and transmitting a second group of ions which subsequently emerges from the separator through the interface with a second different transit time t2.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide is preferably maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

BRIEF DESCRIPTION OF THE DRAWINGS

Various embodiments of the present invention will now be described, by way of example only, and with reference to the accompanying drawings in which.

DETAILED DESCRIPTION OF PREFERRED EMBODIMENTS

Figure 1:
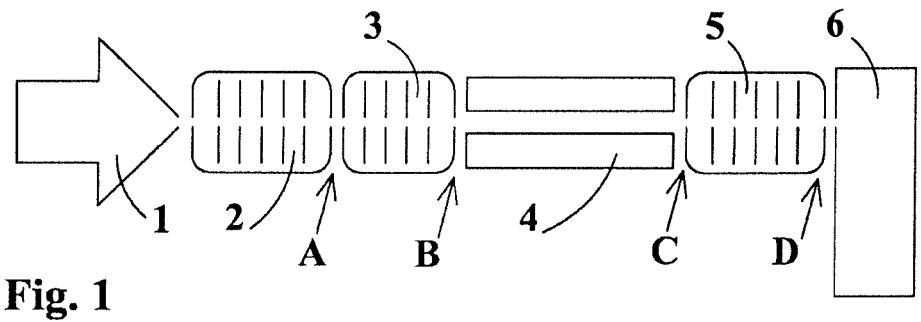
FIG. 1 shows a mass spectrometer according to an embodiment of the present invention comprising an ion mobility spectrometer or separator device, an interface or transfer device, a quadrupole rod set mass filter, a gas cell and an orthogonal acceleration Time of Flight mass analyser.

FIG. 1 shows a simplified schematic of a IMS-Q-ToF mass spectrometer according to an embodiment of the present invention. The mass spectrometer comprises an ion mobility separator ("IMS") 2, an interface or transfer device 3, a quadrupole rod set mass filter 4, a gas or reaction cell 5 and an orthogonal acceleration Time of Flight mass analyser 6. Various different types of experiments may be performed utilising this instrument geometry. In particular, the quadrupole mass filter 4 which is preferably arranged downstream of the ion mobility spectrometer or separator device 2 may be utilised to select specific parent or precursor ions.

According to an embodiment ions may be separated according to their ion mobility in the ion mobility spectrometer or separator device 2. The ions are then preferably transported through the interface, transfer device or transfer region 3 to the quadrupole mass filter 4 which is preferably arranged to operate in a resolving mode. The quadrupole mass filter 4 preferably switches between components of interest which elute from the ion mobility spectrometer or separator device 2 within a single ion mobility spectrometer or separator cycle or single cycle of separation thereby providing both improved selectivity (due to the partially orthogonal nature of ion mobility and mass to charge ratio separations) and also improved duty cycle (due to the temporal pre-separation of the ions before quadrupole filtering). This approach provides significant improvements over standard MSMS approaches for both targeted experiments where the mass to charge ratio and ion mobility of components of interest are derived from a library/method development stage and also for Data Dependent Acquisitions ("DDA") where the mass to charge ratio and ion mobility are derived from an initial survey scan.

Figure 2:
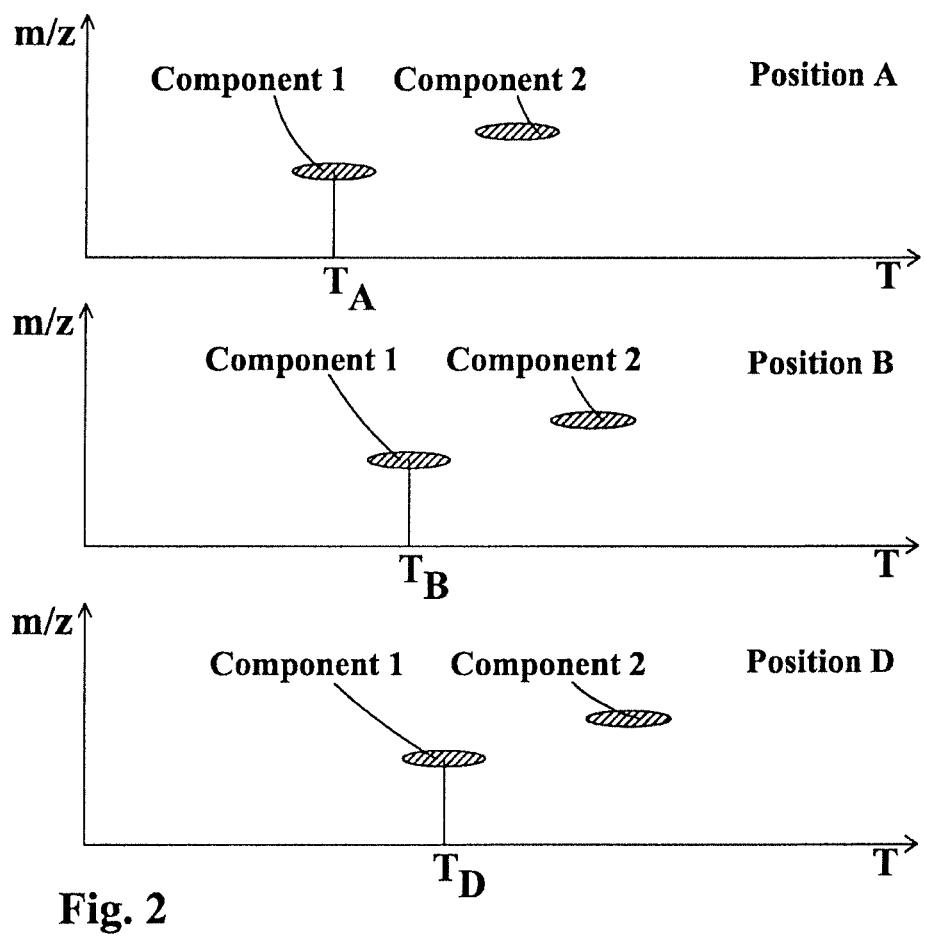
FIG. 2 shows the temporal separation of two ions of interest with respect to the start of an ion mobility experiment at positions A, B and D as shown in FIG. 1.

FIG. 2 shows the temporal separation of two ions of interest with respect to the start of an ion mobility experiment at positions A, B and D within a mass spectrometer as shown in FIG. 1 during a single cycle of separation.

In FIG. 2 the time taken by ions to reach position A is dominated by the mobility of the ions. The ion mobility provides a mechanism of separation as shown by the temporal separation of the two components. The two components of interest also have different mass to charge ratio values as shown in FIG. 2 although, at position A, no mass to charge ratio based separation has yet occurred.

On exiting the ion mobility spectrometer or separator region 2 the ions preferably enter an interface or transfer region 3 which according to an embodiment may comprise a travelling wave ion guide ("TWIG"). The interface or transfer region 3 is preferably maintained at an intermediate pressure between that of the ion mobility spectrometer or separator device 2 and the quadrupole mass filter 4. The travelling wave ion guide preferably transports ions at a fixed velocity such that the times at position B are further increased by a value $T_B-T_A$ which is related to the length of the travelling wave ion guide and the speed of the travelling wave. For example, a 50 mm long travelling wave ion guide operated with a travelling wave speed of 300 m/s would introduce a temporal shift of approximately 167 μs. Again, at this position within the instrument no mass to charge separation has yet occurred.

A similar time shift is observed for ions transiting the gas cell 5 to reach position D although the ions at this point may comprise fragment ions related to components 1 and 2 and at a similar time to components 1 and 2. For illustrative purposes only the two components shown in FIG. 2 have not undergone fragmentation. As the ions transit between position B and position C they preferably pass through a resolving quadrupole mass filter 4 that preferably sequentially isolates the mass to charge ratios of components 1 and 2 at the appropriate times thereby improving selectivity and duty cycle.

The above described approach affords significant advantages over conventional systems. However, it does nonetheless suffer from some limitations. The present invention seeks to address some of these limitations.

One drawback with the approach described above with reference to FIG. 1 is that the ion mobility spectrometer or separator separation times between two closely eluting components may be significantly shorter than the speed at which the resolving quadrupole mass filter 4 can switch between two mass to charge ratio settings.

The time taken to switch a quadrupole mass filter 4 between different mass to charge ratio settings depends on a number of parameters including the settling time of various electronic components and the time of flight through the resolving quadrupole mass filter 4. Typical values for this switching time are of the order of 1 ms. By contrast, two baseline resolved components with nominal transit times through a linear drift tube ion mobility spectrometer or separator device of 5 ms and which operates at a resolution of 50 might be separated in time by only 200 μs. It will be apparent, therefore, that the quadrupole 4 may be unable to switch mass to charge ratio transmission windows on this timescale.

Figure 3:
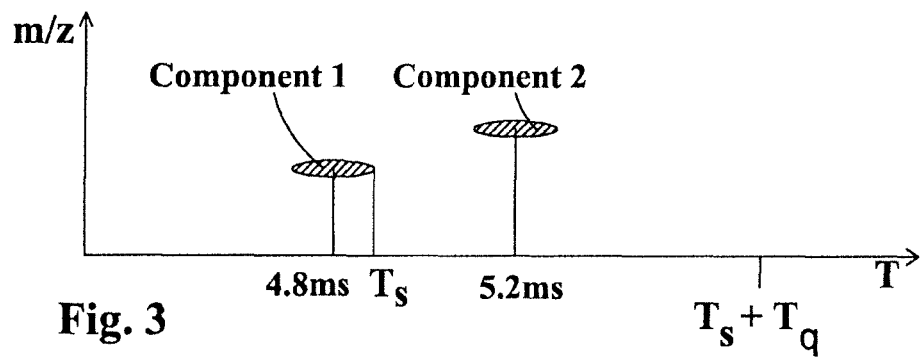
FIG. 3 shows how the difference in timescale between the separation of ions using an ion mobility spectrometer or separator device and the ability to switch a quadrupole mass filter can limit the effectiveness of the isolation stage.

FIG. 3 illustrates in more detail how the difference in timescale between the ion mobility spectrometer or separator device 2 and the switching of the quadrupole mass filter 4 can limit the effectiveness of the isolation stage. FIG. 3 shows a system operating at an approximate ion mobility spectrometer or separator resolution of 50 (FWHM) and shows two components arriving at position B (i.e. at the exit of the ion mobility spectrometer or separator device 2) with nominal transit times of 5 ms. However, the two components are actually separated by 0.4 ms and are therefore fully baseline resolved. The quadrupole mass filter 4 is switched at a time $T_s$ immediately after the last of component 1 has eluted from the ion mobility spectrometer or separator device 2. However, the time taken for the quadrupole mass filter 4 to switch mass to charge ratio transmission windows in order to select between these two components is $T_q$ and it is apparent from FIG. 3 that component 2 will arrive at the quadrupole mass filter 4 before time $T_s+T_q$. As a result, component 2 will arrive at the mass filter 4 before the mass filter 4 has had sufficient time to switch to transmit ions having mass to charge ratios corresponding with component 2. As a result, component 2 will not be onwardly transmitted by the mass filter 4. This effectively limits the resolution of the filtering or isolation stage.

According to an embodiment of the present invention an improvement to this approach is to delay component 2 by introducing an interface or transfer device 3 between the ion mobility spectrometer or separator device 2 and the quadrupole mass filter 4 and by altering the transit time across or through the interface or transfer region 3 during a single cycle of separation. This may be achieved by, for example, altering (i.e. reducing) the speed of a travelling wave applied to the interface or transfer ion guide 3 after component 1 has exited or emerged from the interface or transfer device 3 during a single cycle of separation.

Figure 4:
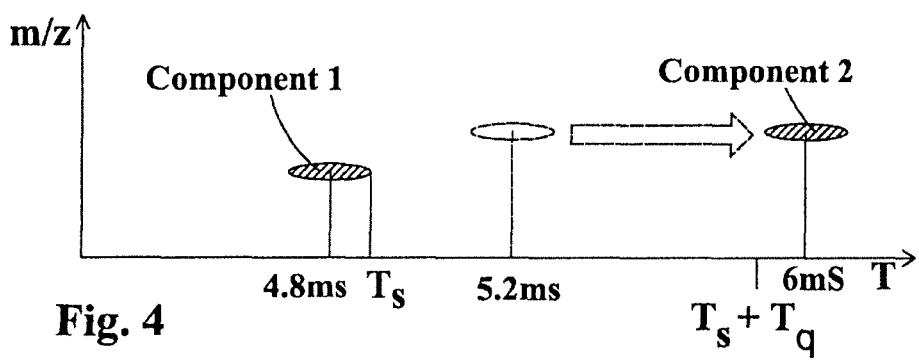
FIG. 4 illustrates the effect of increasing the transit time of ions through an interface or transfer region in accordance with a preferred embodiment of the present invention.

FIG. 4 shows the effect of reducing the speed of the travelling wave applied to electrodes of the interface from 300 m/s to 60 m/s after component 1 has exited the interface or transfer travelling wave ion guide 3. For a transfer travelling wave ion guide 3 having a length of 50 mm the transit time for component 2 to traverse the interface or transfer travelling wave ion guide 3 is increased by 833 μs. This shift or increase in transit time ensures that component 2 will now arrive at the quadrupole mass filter 4 after the quadrupole mass filter 4 has switched and has had sufficient time to settle thereby ensuring onward transmission of component 2. In this case the resolution of the isolation stage is now related to the transit time through the interface or transfer device 3.

It is worth noting that the separation in time for a given ion mobility spectrometer or separator resolution can be significantly different for ion mobility spectrometer or separator instruments not using linear drift tubes such as T-Wave based ion mobility spectrometer or separator devices depending on the power term (X) in the relationship $T=A \times K^X$ where T is the drift time, K is the mobility and A is a constant. This difference can either aid or hinder the effects of previously described quadrupole switching limitation.

A second drawback of the approach described above with reference to FIG. 3 is that the ion mobility separation also introduces significant restrictions to the dynamic range of the ion detecter system of an IMS-Q-ToF mass spectrometer due to the compression in time of any given component and the limited intensity scale of the ion detection system digitisation.

Figure 5:
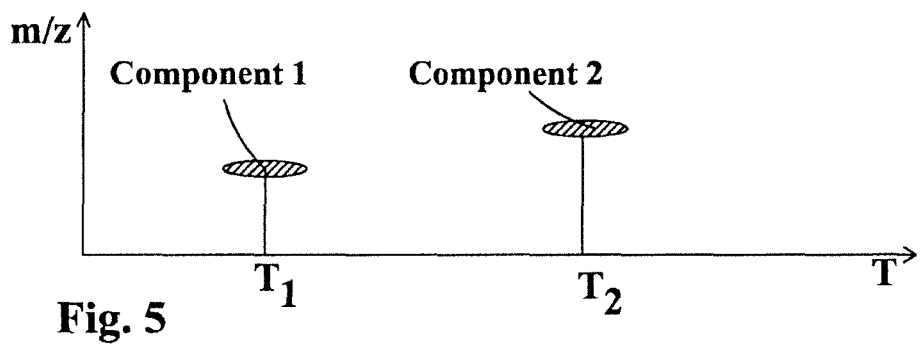
FIG. 5 shows two components separated at the exit of the gas cell.

FIG. 5 shows two components which are well separated and isolated in IMS-mass to charge ratio space at position D in FIG. 1 i.e. at the exit of the gas cell 5.

Figure 6:
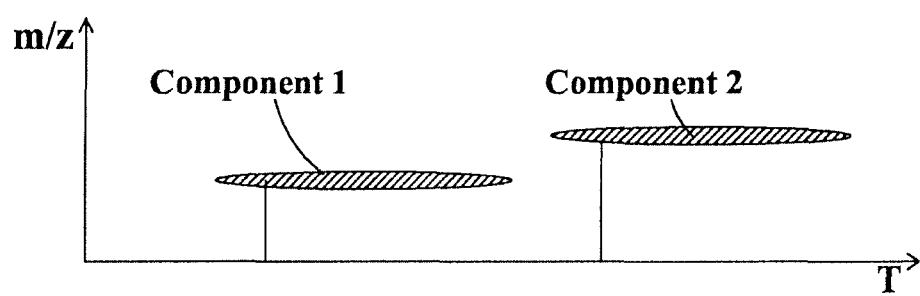
FIG. 6 shows how according to an embodiment the gas cell may be configured to allow some loss of fidelity of the IMS peaks in order to improve dynamic range.

According to a further embodiment the gas cell 5 may be configured to allow some loss of fidelity of the ion mobility spectrometer or separator peaks as shown in FIG. 6. As a result, a greater number of orthogonal acceleration Time of Flight pushes are now used to analyse the components. This advantageously increases the dynamic range of the system. The choice of the degree of loss of fidelity can be based on degree of separation of the two components.

In both of the above examples the choice of two components is for descriptive purposes only. In practice, more than two components may be chosen depending on separations or resolution etc.

Ions which are onwardly transmitted may be subjected to analytical techniques such as fragmentation, mass measurement or ion mobility measurement etc.

Further embodiments are contemplated wherein the described approach is applied with other fast pre quadrupole separators such as ion traps and mass to charge ratio separators.

According to another less preferred embodiment instead of switching the transit delay in time, ions may alternatively be switched in space into different transfer devices each having different effective transit times.

According to another embodiment transfer devices 3 utilising approaches other than travelling waves such as axial fields may be used.

Other instrument improvements can be accessed via the approach according to the preferred embodiment. For example, components can be pushed together in time if they are over separated allowing shorter ion mobility spectrometer or separator cycle times thereby ultimately reducing space charge effects in pre ion mobility spectrometer or separator accumulators.

The delay shifts may be introduced by devices operating at the same pressure as the ion mobility spectrometer or separator device 2.

The delay shifts can also be introduced by altering the parameters of the ion mobility spectrometer or separator device 2 itself.

A continuous stretching of the time axis may be realised by continually and monotonically slowing the travelling wave speed so as to improve the ability of a scanning quadrupole mass filter 4 to track ions eluting from the ion mobility spectrometer or separator device 2 or to improve the digitisation of the ion mobility spectrometer or separator device 2 by, for example, the orthogonal acceleration Time of Flight mass analyser 6.

Transfer devices 3 with transit speeds that vary as a function of length may be utilised as well as transfer devices with accumulation regions.

Figure 7:
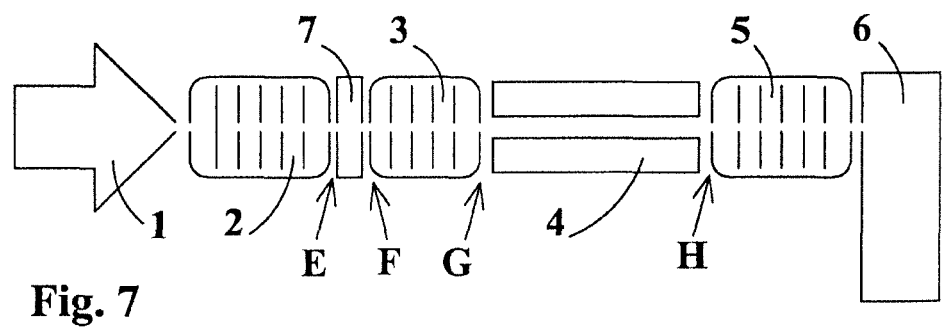
FIG. 7 shows a further embodiment wherein an ion gate is provided upstream of the interface or transfer device.

The quadrupole mass filter 4 preferably provides isolation in both time and mass to charge ratio. However, in practice different devices may be used to provide time isolation (e.g. an ion gate 7) and mass to charge ratio isolation (e.g. a quadrupole mass filter 4). FIG. 7 shows a schematic of an example of this type of geometry.

In the embodiment shown in FIG. 7 time regions corresponding to the regions containing components of interest are selected by the ion gate 7. The ion gate 7 may be part of the ion mobility spectrometer or separator device 2 or the transfer device 3 and is shown in FIG. 7 as a separate component for illustrative purpose only. The time selected regions may then be partitioned by the transfer travelling wave ion guide 3 and their temporal separations adjusted as they transit the transfer travelling wave ion guide 3 so as to allow efficient delivery to the resolving quadrupole mass filter 4. The previously described position dependent travelling wave speed travelling wave ion guide with accumulation regions is particularly beneficial for this approach.

Although the present invention has been described with reference to preferred embodiments, it will be understood by those skilled in the art that various changes in form and detail may be made without departing from the scope of the invention as set forth in the accompanying claims.

The invention claimed is:

1. An analytical device for analysing ions comprising:
   a separator for separating ions according to a physico-chemical property;
   an interface comprising one or more ion guides, each ion guide comprising a plurality of electrodes;
   a mass or mass to charge ratio filter arranged downstream of said interface; and
   a control system arranged and adapted:
   (i) to transmit a first group of ions which emerges from said separator through said interface with a first transit time t1; and
   (ii) to transmit a second group of ions which subsequently emerges from said separator through said interface with a second different transit time t2.

2. An analytical device as claimed in claim 1, wherein said control system is arranged and adapted to transmit said first group of ions which emerges from said separator through said interface with a first transit time t1 and to transmit said second group of ions which subsequently emerges from said separator through said interface with a second different transit time t2 within or during a single cycle of separation of ions within said separator.

3. An analytical device as claimed in claim 1, wherein said physico-chemical property comprises ion mobility or differential ion mobility.

4. An analytical device as claimed in claim 3, wherein said separator comprises an ion mobility separator or a differential ion mobility separator.

5. An analytical device as claimed in claim 1, wherein said physico-chemical property comprises mass or mass to charge ratio.

6. An analytical device as claimed in claim 5, wherein said separator comprises a time of flight region.

7. An analytical device as claimed in claim 1, wherein said control system is arranged and adapted to transmit said second group of ions through said interface with a transit time t2, wherein t2>t1.

8. An analytical device as claimed in claim 1, wherein said control system is further arranged and adapted to apply one or more transient DC voltages or potentials to said plurality of electrodes so that said first group of ions are translated along said one or more ion guides with a first velocity.

9. An analytical device as claimed in claim 8, wherein said control system is further arranged and adapted to apply one or more transient DC voltages or potentials to said plurality of electrodes so that said second group of ions are translated along said one or more ion guides with a second different velocity.

10. An analytical device as claimed in claim 9, wherein said second different velocity is slower than said first velocity.

11. An analytical device as claimed in claim 1, wherein said control system is further arranged and adapted to maintain at a first time a first DC voltage or potential gradient along said one or more ion guides so that said first group of ions are urged along said one or more ion guides with a first velocity.

12. An analytical device as claimed in claim 11, wherein said control system is further arranged and adapted to maintain at a second later time a second DC voltage or potential gradient along said one or more ion guides so that said second group of ions are urged along said one or more ion guides with a second different velocity.

13. An analytical device as claimed in claim 12, wherein said second DC voltage or potential gradient is less than said first DC voltage or potential gradient.

14. An analytical device as claimed in claim 1, wherein said control system is further arranged and adjusted:
   (i) to cause said mass or mass to charge ratio filter to transmit ions having masses or mass to charge ratios within a first mass or mass to charge ratio range; and then
   (ii) to cause said mass or mass to charge ratio filter to transmit ions having masses or mass to charge ratios within a second different mass or mass to charge ratio range.

15. A mass spectrometer comprising an analytical device as claimed in claim 1.

16. A method of analysing ions comprising:
   separating ions according to a physico-chemical property in a separator;

providing an interface comprising one or more ion guides, each ion guide comprising a plurality of electrodes and a mass or mass to charge ratio filter arranged downstream of said interface;

transmitting a first group of ions which emerges from said separator through said interface with a first transit time t1; and transmitting a second group of ions which subsequently emerges from said separator through said interface with a second different transit time t2.

17. A method as claimed in claim 16, wherein the steps of transmitting said first group of ions which emerges from said separator through said interface with a first transit time t1 and transmitting said second group of ions which subsequently emerges from said separator through said interface with a second different transit time t2 are performed within or during a single cycle of separation of ions within said separator.

18. A method of mass spectrometry comprising a method as claimed in claim 16.

19. An analytical device for analysing ions comprising:
a separator for separating ions according to a physico-chemical property;
an interface;
a mass or mass to charge ratio filter arranged downstream of said interface; and
a control system arranged and adapted:
(i) to transmit a first group of ions which emerges from said separator through a first ion path through said interface with a first transit time t1; and
(ii) to transmit a second group of ions which subsequently emerges from said separator through a second different ion path through said interface with a second different transit time t2.

20. An analytical device as claimed in claim 19, wherein said control system is arranged and adapted to transmit said first group of ions which emerges from said separator through a first ion path through said interface with a first transit time t1 and to transmit a second group of ions which subsequently emerges from said separator through a second different ion path through said interface with a second different transit time t2 within or during a single cycle of separation of ions within said separator.

21. A method of analysing ions comprising:
separating ions according to a physico-chemical property in a separator;
providing an interface and a mass or mass to charge ratio filter arranged downstream of said interface;
transmitting a first group of ions which emerges from said separator through a first ion path through said interface with a first transit time t1; and
transmitting a second group of ions which subsequently emerges from said separator through a second different ion path through said interface with a second different transit time t2.

22. A method as claimed in claim 21, wherein the steps of transmitting said first group of ions which emerges from said separator through a first ion path through said interface with a first transit time t1 and transmitting a second group of ions which subsequently emerges from said separator through a second different ion path through said interface with a second different transit time t2 are performed within or during a single cycle of separation of ions within said separator.

* * * * *